(12) United States Patent
Li et al.

(10) Patent No.: US 10,687,821 B2
(45) Date of Patent: Jun. 23, 2020

(54) LUNG VOLUME REDUCTION ELASTIC IMPLANT AND LUNG VOLUME REDUCTION INSTRUMENT

(71) Applicant: Lifetech Scientific (Shenzhen) Co., Ltd., Shenzhen (CN)

(72) Inventors: Anning Li, Shenzhen (CN); Siyi Li, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 10 days.

(21) Appl. No.: 15/776,050

(22) PCT Filed: Jun. 29, 2016

(86) PCT No.: PCT/CN2016/087790
§ 371 (c)(1),
(2) Date: May 14, 2018

(87) PCT Pub. No.: WO2017/084347
PCT Pub. Date: May 26, 2017

(65) Prior Publication Data
US 2018/0333157 A1    Nov. 22, 2018

(30) Foreign Application Priority Data

Nov. 16, 2015    (CN) .......................... 2015 1 0785463

(51) Int. Cl.
*A61B 17/12*    (2006.01)
*A61F 2/04*    (2013.01)
(Continued)

(52) U.S. Cl.
CPC .... *A61B 17/12104* (2013.01); *A61B 17/1214* (2013.01); *A61B 90/39* (2016.02);
(Continued)

(58) Field of Classification Search
CPC .............. A61B 2017/0089; A61B 2018/00541
(Continued)

(56) References Cited

U.S. PATENT DOCUMENTS 8,632,605 B2 *  1/2014  Thompson ....... A61B 17/12022
                                                        623/23.65
8,721,734 B2 *  5/2014  Mathis ................. A61B 1/2676
                                                        623/23.65
(Continued)

FOREIGN PATENT DOCUMENTS

CN        202010169 U       10/2011
CN        102573700 A        7/2012
(Continued)

OTHER PUBLICATIONS

International Search Report dated Sep. 21, 2016 for corresponding PCT Application No. PCT/CN2016/087790.
(Continued)

*Primary Examiner* — Suzette J Gherbi
(74) *Attorney, Agent, or Firm* — Raymond Sun

(57) ABSTRACT

Disclosed are a lung volume reduction elastic implant and a lung volume reduction device, wherein the lung volume reduction elastic implant (500) is tubular and at least opens at the proximal end thereof, and comprises an elastic deformation section (51), a flexible guide section (53) connected to the distal end of the elastic deformation section (51), and a protuberance (571) connected to the proximal end of the elastic deformation section (51), wherein the elastic deformation section (51) has shape memory characteristics and has several grooves (514) arranged at intervals along the length direction, each groove (514) connecting with the lumen of the elastic deformation section (51). Under the same external force, the flexible guide section (53) deforms more easily than the elastic deformation section (51), the outer diameter of the protuberance (571) is larger than the
(Continued)

outer diameter of the elastic implant (500) in the delivery state when same is close to the protuberance (571), and the device delivers the implant without a delivery sheath, thereby preventing the delivery sheath from causing damage to the inner wall of the bronchus and reducing the incidence of pneumothorax.

20 Claims, 16 Drawing Sheets

(51) Int. Cl.
*A61B 90/00* (2016.01)
*A61B 17/00* (2006.01)

(52) U.S. Cl.
CPC ............. *A61B 17/12145* (2013.01); *A61B 2017/00477* (2013.01); *A61B 2017/00809* (2013.01); *A61B 2017/00862* (2013.01); *A61B 2017/00867* (2013.01); *A61B 2017/1205* (2013.01); *A61B 2017/12095* (2013.01); *A61B 2090/3966* (2016.02); *A61F 2/04* (2013.01); *A61F 2002/043* (2013.01)

(58) Field of Classification Search
USPC .................................................. 623/23.65, 9
See application file for complete search history.

(56) References Cited

U.S. PATENT DOCUMENTS

| | | | |
|---|---|---|---|
| 9,402,633 B2* | 8/2016 | Vasquez | A61B 17/12104 |
| 10,342,549 B2* | 7/2019 | Lin | A61F 2/844 |
| 2009/0012626 A1* | 1/2009 | Thompson | A61B 17/12022 |
| | | | 623/23.65 |
| 2014/0358140 A1* | 12/2014 | Emmons | A61B 18/1815 |
| | | | 606/33 |
| 2015/0051709 A1* | 2/2015 | Vasquez | A61B 17/12104 |
| | | | 623/23.65 |
| 2015/0073563 A1* | 3/2015 | Mathis | A61B 1/2676 |
| | | | 623/23.65 |
| 2018/0132860 A1* | 5/2018 | Lin | A61F 2/844 |
| 2018/0303593 A1* | 10/2018 | Li | A61F 2/04 |
| 2018/0325592 A1* | 11/2018 | Emmons | A61B 18/1815 |

FOREIGN PATENT DOCUMENTS

| | | |
|---|---|---|
| CN | 103860299 A | 6/2014 |
| CN | 105455930 | 4/2016 |
| CN | 106580527 A | 4/2017 |
| WO | WO2014151557 A2 | 9/2014 |

OTHER PUBLICATIONS

Office Action dated Oct. 31, 2017 for corresponding China Application No. 201510785463.8.

* cited by examiner

LUNG VOLUME REDUCTION ELASTIC IMPLANT AND LUNG VOLUME REDUCTION INSTRUMENT

TECHNICAL FIELD

The present disclosure belongs to the technical field of interventional therapy, relates to an implant and a device for the interventional therapy, and particularly relates to a lung volume reduction elastic implant and a lung volume reduction device.

BACKGROUND ART

Pulmonary emphysema is a common pulmonary disease. Traditional internal therapies for pulmonary emphysema include oxygen inhalation, pulmonary infection prevention, bronchus spasm relaxation and the like, but the curative effect is extremely limited. Surgical therapies for pulmonary emphysema mostly adopt lung volume reduction surgery, and there are also many limitations, for example: strict surgical indications, risks of many complications, anesthesia and anesthesia-related complications, difficulty in curative effect prediction before the surgery, and an irreparable non-ideal curative effect caused by over-cutting or sub-cutting after the surgery, excessively high surgical costs, and great mental and physical sufferings. In addition, some patients cannot always tolerate the surgery due to their poor lung functions, which leads to a higher postoperative mortality rate, thereby limiting the application of surgery.

In order to better treat pulmonary emphysema, to improve quality of life for a patient, and to reduce traumas to the patient during surgery, international research has tried to use a bronchoscope to implement interventional modes such as a one-way valve, biogel, steam thermal ablation, and elastic coils for treating pulmonary emphysema. However, the one-way valve has been rejected by the FDA (Food and Drug Administration) in the United States due to its low clinical indicators that residual gas and sputum in a target region cannot be effectively and actively excreted, and technical difficulties in collateral ventilation and precise placement of the one-way valve at different anatomical structural positions also limit the curative effectiveness of the one-way valve. The problem with the biogel completely blocking an emphysema region and leading to postoperative inflammation is still unsolved. Steam thermal ablation often leads to postoperative inflammation due to a defect of destroying an original tissue structure of the emphysema region.

At the present, an updated therapy method is being adopted for pulmonary emphysema, where an elastic coil serving as an implant is implanted into a lesion portion of the lung of a human body. FIG. 1 is a schematic diagram of a lung volume reduction elastic coil in the prior art. This product is designed and made of a nickel-titanium memory alloy metal wire, and may elastically deform under the action of an external force. Under the restriction of a loading system, this product may be implanted into a lung through a working channel of a bronchoscope in a straight line configuration. After being delivered into a bronchus of a pulmonary emphysema region, the coil is released from the restriction of the loading system and then recovers to its natural shape (which is a shape without the external force) as shown in FIG. 1, and at the same time, the emphysema region is squeezed under the pulling action of the nickel-titanium alloy wire, thereby discharging gas in the bronchus and reducing the volume of a lung tissue in the pulmonary emphysema region. This results in a relatively healthy lung tissue therearound that can provide a better physiological function.

A surgical method using the elastic coil includes three operation processes of inserting a bronchoscope, building a channel and implanting a product. Insertion of the bronchoscope is as shown in FIG. 2: a bronchoscope 201 is inserted through a mouth or a nose, and may display an image detected by the distal end 203 of the bronchoscope 201 on a monitor 204, thereby guiding the bronchoscope 201 to reach the bronchus 205 of a human lung.

Building of the channel is as shown in FIG. 2. The outer diameter of a guide wire 206 is about 5 Fr to 7 Fr, and the diameter of a delivery sheath may be about 5 Fr to 9 Fr. The guide wire 206 is moved to pass through an inner cavity of an expander 207, and the expander 207 is moved to pass through an inner cavity of the delivery sheath 208; after being assembled, the guide wire 206, the expander 207 and the delivery sheath 208 enter the bronchoscope 201 together from a working channel 202 of the bronchoscope 201, and then pass through the distal end 203 of the bronchoscope 201 and enter the bronchus 205. A length label 210 is disposed at the distal end 209 of the guide wire 206, and indicates a distance along the guide wire 206 from the distal end 209. The distal end 211 of the delivery sheath 208 may have multiple corresponding labels 210 in the form of high-contrast metal straps (including gold, platinum, tantalum, iridium, tungsten and/or metalloids). A fluorescence inspection system, an ultrasonic imaging system, an MRI (Magnetic Resonance Imaging) system, or an X-ray CT (Computerized Tomography) system, which are provided with a remote imaging and capturing device 212, or some other remote imaging implants, are configured to guide the guide wire 206. As shown in FIG. 2, the remote imaging and capturing device 212 may display a detected image on a monitor 213, and identify a track of the guide wire 206 or an imaging label 210, thereby building the channel.

After the channel is built, the expander 207 and the guide wire 206 are pulled out towards the proximal end from the delivery sheath 208, so that a lung volume reduction elastic coil 301 may be loaded in an open cavity of the delivery sheath 208. Implantation of the coil 301 is shown in FIG. 3, and the loading system 302 with the coil 301 is connected to the proximal end of the delivery sheath 208 through a locking hub connector 303. The coil 301 is introduced into the delivery sheath, as shown in FIG. 4, and a steel cable 305 of an actuation device 304 pushes the product out of the distal end of the delivery sheath 208 and enables the product to enter the bronchus 205. Then the delivery sheath 208 is withdrawn, and a gripper 306 of the actuation device 304 is configured to release the coil 301. When recovering to its initial shape, the coil 301 also pulls the bronchus 205 to be in a curled shape, thereby achieving a pulmonary emphysema volume reduction treatment effect.

The above-mentioned implant and its implantation method have the following defects:

1. An elastic coil is required to be released through a delivery sheath which may injure the inner wall of a bronchus during its pushing in the bronchus and cause adverse events such as pneumothorax.

2. As the delivery sheath has a relatively large outer diameter of about 5 Fr to 9 Fr, it is really difficult to implant the elastic coil into a lung bypass or the ends of some small-diameter tracheas, and only a limited pulmonary emphysema region is squeezed and pulled by the elastic coil, thereby affecting the volume reduction effect.

3. The existing surgical method for implanting an elastic coil requires three independent operation processes of inserting the bronchoscope, building the channel and implanting the product, so that a relatively long operation time is needed. In addition, as the surgery is conducted when a patient is awake, extremely long operation time may easily lead to adverse events such as discomfort of the patient and acute exacerbation of a COPD (Chronic Obstructive Pulmonary Disease).

SUMMARY OF THE INVENTION

In order to solve the technical problems, in view of the above-mentioned defects in the prior art, the present disclosure provides an implant which is directly delivered through a core wire instead of a delivery sheath. The adoption of the implant may prevent the delivery sheath from injuring the inner wall of a bronchus and reduce incidences of pneumothorax.

In order to further solve the technical problem, the present disclosure provides a lung volume reduction device which may implant the implant into a lung bypass or the ends of some small-diameter tracheas according to an actual clinical requirement, integrate a channel building process with an implant implantation operation process, make surgical operation more convenient, shorten the surgical operation time, and achieve a better treatment effect.

A technical scheme adopted by the present disclosure to solve the technical problems is as follows:

A lung volume reduction elastic implant is provided, which is tubular and is opened at least at the proximal end. The implant includes an elastic deformation section, a flexible guide section connected with the distal end of the elastic deformation section, and a protuberance connected with the proximal end of the elastic deformation section. The elastic deformation section has a shape memory characteristic and has a plurality of grooves formed in a spaced manner along its lengthwise direction. Each groove is communicated with a lumen of the elastic deformation section. Under the action of the same external force, the flexible guide section deforms more easily than the elastic deformation section, and the outer diameter of the protuberance is larger than that of a portion, which is close to the protuberance, on the elastic implant in a delivery state.

In one embodiment of the technical scheme, an included angle between the incision direction of each groove and the lengthwise direction of the elastic deformation section ranges from 10 to 90 degrees.

In one embodiment of the technical scheme, the implant further includes an elastic film that surrounds the outer walls of the elastic deformation section and the flexible guide section.

In one embodiment of the technical scheme, the grooves are further filled with the elastic film.

In one embodiment of the technical scheme, the elastic deformation section is made of a conical nickel-titanium tube having an outer diameter that gradually increases from the distal end to the proximal end, and a gap of 0.05 mm to 0.5 mm is provided between every two adjacent grooves of the elastic deformation section.

In one embodiment of the technical scheme, under the action of the same external force, the flexible guide section deforms more easily in an increasing manner from the proximal end to the distal end.

In one embodiment of the technical scheme, the flexible guide section includes a main body portion having a spring on the outer wall; the proximal end of the main body portion is connected with the elastic deformation section; and the outer diameter of the main body portion gradually increases from its distal end to proximal end.

In one embodiment of the technical scheme, the flexible guide section includes a tubular body which is cut from the nickel-titanium tube and has continuous spiral grooves.

In one embodiment of the technical scheme, a gap between every two adjacent grooves of the flexible guide section along the axial direction of the flexible guide section gradually increases from the distal end to the proximal end of the flexible guide section.

In one embodiment of the technical scheme, the elastic implant further includes a connection section located between the elastic deformation section and the protuberance. Under the action of the same external force, the connection section deforms more easily than the elastic deformation section.

In one embodiment of the technical scheme, the connection section has a plurality of grooves formed in a spaced manner along its lengthwise direction, and each groove of the connection section communicates with the lumen of the connection section.

In one embodiment of the technical scheme, the connection section includes multiple hollow subcomponents connected with one another in an end-to-end manner. The proximal end of each hollow subcomponent includes multiple proximal end bulges distributed in a circumferential direction of the hollow subcomponent; the circumferential length of each proximal end bulge gradually decreases from the proximal end to the distal end; a proximal end recess is formed between every two adjacent proximal end bulges; the distal end of each hollow subcomponent includes multiple distal end bulges distributed in the circumferential direction of the hollow subcomponent; the circumferential length of each distal end bulge gradually increases from the proximal end to the distal end; and a distal end recess is formed between every two adjacent distal end bulges.

In one embodiment of the technical scheme, the end surface of part of the distal end of the protuberance is sunken towards the proximal end of the protuberance, thereby forming an annular recess surrounding the longitudinal central line of the protuberance.

In one embodiment of the technical scheme, part of the side surface of the protuberance is sunken towards the inside of the protuberance, thereby forming an annular recess surrounding the longitudinal central line of the protuberance.

In one embodiment of the technical scheme, the protuberance includes multiple small bulges distributed in the circumferential direction of the protuberance in a spaced manner.

A lung volume reduction device is provided for use with any one of the above-mentioned implants and a delivery device that is adapted for use with the implant. The delivery device includes a core wire and a hollow pushing member; the implant is detachably connected to the distal end of the pushing member through its proximal end; the core wire may be extended in, and is movably disposed in, a lumen of the implant and a lumen of the pushing member.

In one embodiment of the technical scheme, a core wire guide head coaxial with the core wire is disposed at the distal end of the core wire, and the outer diameter of the core wire guide head is consistent with that of the core wire.

In one embodiment of the technical scheme, the core wire guide head includes a guide post and a spring surrounding the guide post; the guide post and the core wire are made in one piece in an integrated structure or the guide post is fixedly connected to the distal end of the core wire; and the spring has an imaging label.

In one embodiment of the technical scheme, the proximal end of the implant has a detachably threaded connection with the distal end of the pushing member.

Compared with the prior art, an implant of the present disclosure is tubular and is opened at least at its proximal end, and the core wire may be directly inserted into the lumen of the implant to restrict the implant in a straight line configuration for delivery, so that no delivery sheath with a larger outer diameter than the implant is required for restricting the implant, thereby preventing the delivery sheath from injuring the trachea in a delivery process, and further reducing the incidence of pneumothorax.

An implant of the present disclosure has a hollow lumen structure, so that the core wire is conveniently inserted through the lumen of the implant in advance during operation, so that the implant can be disposed on the core wire, and then the implant and the core wire are pushed into the bronchus in a pulmonary emphysema region together through the bronchoscope. In addition, an implant with a core wire further has a function of exploring a path in the bronchus to a lesion region. Therefore, the two operation processes of building the channel and implanting the implant in the prior art are performed synchronously, which may effectively shorten the surgical operation time to avoid adverse events such as acute exacerbation of a COPD (Chronic Obstructive Pulmonary Disease).

Further, the surface of an elastic deformation section of the implant or the surface of the whole implant is wrapped by one elastic film which may avoid direct contact between the metal surface of the implant and the inner wall of the bronchus, thereby reducing the release of metal elements and effectively reducing the chances of pneumonia or small airway infections.

According to the lung volume reduction device of the present disclosure, a core wire is configured to load an implant, guide the building of the channel, deliver the implant, and release it; or a guide head is disposed at the distal end of an implant, which also plays a role in guiding and building a channel, and may release the implant immediately after the channel is built; and this scheme is configured to integrate the channel building process with the implant implantation operation process, so that the surgical operation is more convenient, and the surgical operation time is further shortened.

According to the lung volume reduction device of the present disclosure, the delivery device inserts a core wire through an implant having a lumen structure, and completes delivery of the implant through pushing of a pushing mechanism. Under the restriction of a core wire, an implant turns into a delivery state (namely, a straight line configuration matched with the shape of a core wire) from a natural state (namely, a preset curled state obtained by thermal treatment); after the core wire is withdrawn from the lumen of an implant, the restriction of the core wire is relieved, so that the implant may return into the natural state from the delivery state, achieving the effect of squeezing a target pulmonary emphysema region. Compared with a delivery sheath in the prior art, the delivery device of the present disclosure has no delivery sheaths, so that the diameter is smaller, and the implant may enter a smaller target pulmonary emphysema region to achieve a better treatment effect. By adopting the technical scheme of combining channel building and implant releasing, the present disclosure may shorten the entire surgical time, and may be located in the target pulmonary emphysema region more precisely.

According to the lung volume reduction device of the present disclosure, the surface of an implant is further wrapped by one elastic film which is made of a macromolecular material having a higher biocompatibility, so that the elastic film made of the macromolecular material is in contact with the inner wall of the bronchus. Compared with the prior art scheme where a nickel-titanium wire is in direct contact with the inner wall of the bronchus, a lung volume reduction device of the present disclosure reduces bronchial inflammation and injury caused by friction between the implant and the inner wall of the bronchus in a respiration process, thereby reducing the risks of pneumonia and small airway infections. In addition, wrapping the metal surface of the implant with the elastic film made of the macromolecular material may effectively reduce the release of metal elements.

BRIEF DESCRIPTION OF THE DRAWINGS

A further description for the present disclosure in combination with drawings and embodiments is as follows. In the drawings.

DETAILED DESCRIPTION OF THE INVENTION

For the purpose of making the objects, features and advantages of the present disclosure clearer, a detailed description for specific implementation modes of the present disclosure with drawings is as follows. Many specific details are specified in descriptions as follows to facilitate a full understanding of the present disclosure. However, the present disclosure may be implemented through many other modes different from those described herein. A person skilled in the art can make similar improvements without departing from the subject matter of the present disclosure, thus the present disclosure should not be limited by the specific embodiments disclosed as follows.

In the field of intervention, generally, an end relatively close to an operator is called a proximal end, and an end relatively far away from the operator is called a distal end.

Unless otherwise defined, all technical and scientific terms used herein have the same meanings of general understandings of persons skilled in the art of the present disclosure. Terms used in the description of the present disclosure herein are only intended to describe the specific embodiments, but not to limit the present disclosure. Terms "and/or" used herein include any and all combinations of one or multiple relevant listed items.

Figure 1:
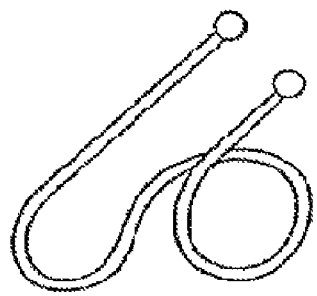
FIG. 1 is a structural schematic diagram of an elastic coil in a prior art.
Figure 2:
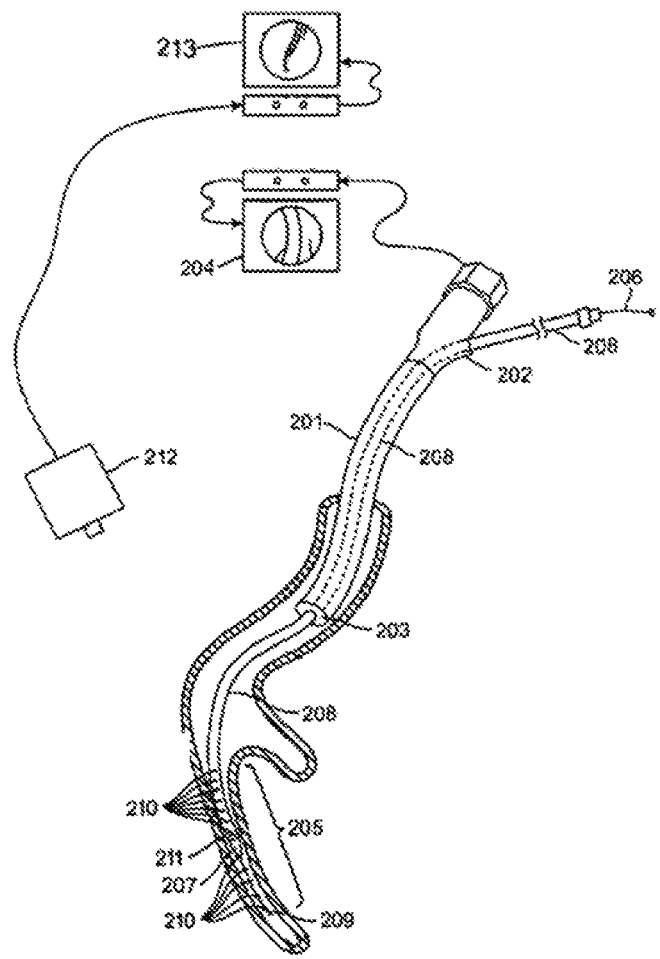
FIG. 2 is an operation schematic diagram showing the implantation of a bronchoscope and the building of a channel through a core wire in the prior art.
Figure 3:
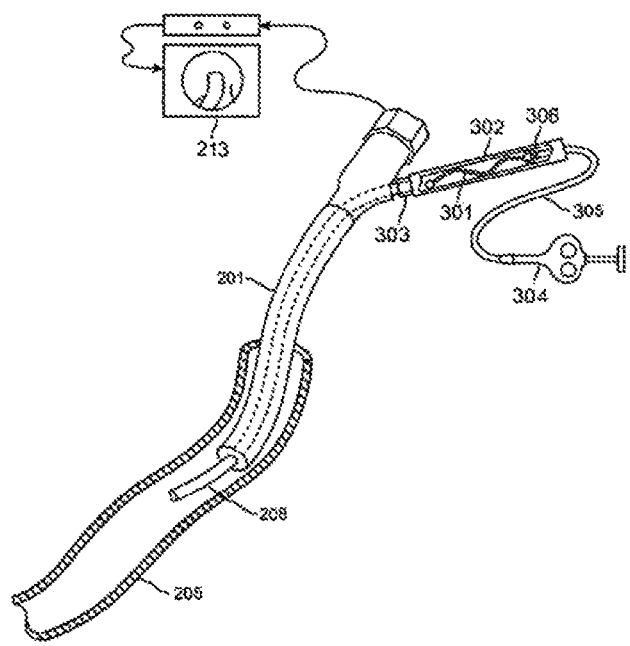
FIG. 3 is a schematic diagram of the delivery of an elastic coil in the prior art.
Figure 4:
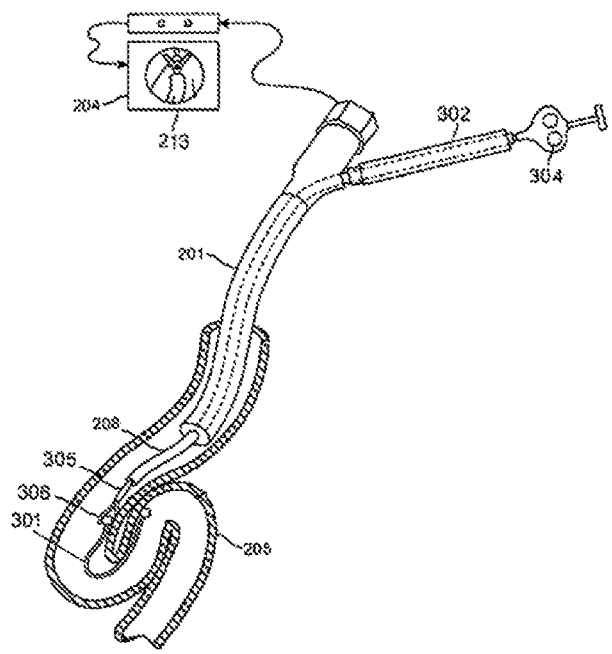
FIG. 4 is a schematic diagram of release of an elastic coil in the prior art.
Figure 5:
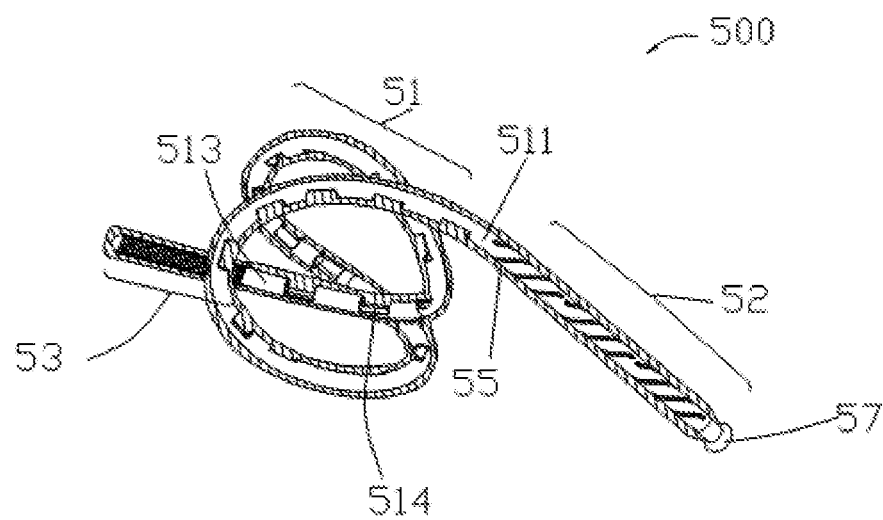
FIG. 5 is a schematic diagram of an implant, on which part of a film is torn away, provided by one embodiment of the present disclosure.
Figure 6:
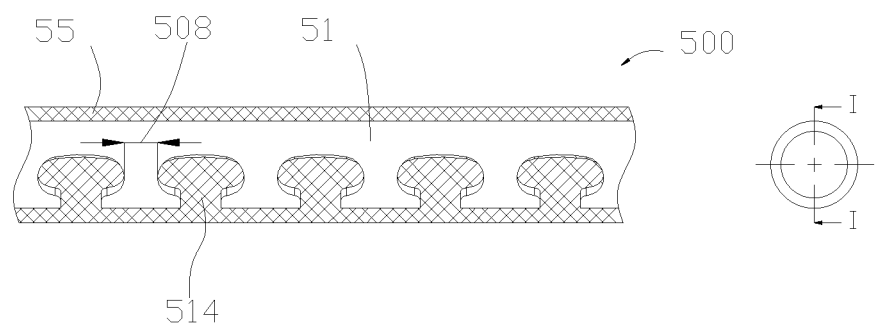
FIG. 6 is a sectional view of part of the implant in FIG. 5.

With reference to FIG. 5 and FIG. 6, an elastic implant 500 provided by one embodiment of the present disclosure is of a tubular structure, which includes a hollow tubular elastic deformation section 51, a flexible guide section 53 connected with the distal end of the elastic deformation section 51, a connection section 52 connected with the proximal end of the elastic deformation section 51, a connection member 57 connected with the proximal end of the connection section 52, and an elastic film 55. The implant 500 is opened at least at the proximal end; the elastic deformation section 51 and the flexible guide section 53 may be made in one piece in an integrated structure, or are fixedly connected with each other. The distal end of the flexible guide section 53 is the distal end of the elastic implant 500. Under the action of the same external force, the flexible guide section 53 deforms more easily than the elastic deformation section 51 (i.e., under the action of the same external force, the bending resistance of the flexible guide section 53 is lower than that of the elastic deformation section 51), so that it may experience better movement in a bronchus without injuring a surrounding tissue.

The elastic deformation section 51 has a shape memory characteristic, and includes a proximal end 511 and an opposite distal end 513; and the distal end 513 is connected with the flexible guide section 53. The elastic deformation section 51 further includes multiple grooves 514 which are isolated from one another and which communicate with a lumen of the elastic deformation section 51. The multiple grooves 514 enable the elastic deformation section 51 of the elastic implant 500 to be bent into a preset shape in a natural state, for example, a shape as shown in FIG. 5.

In the natural state (namely without any external force), the elastic deformation section 51 is of a preset curled shape, but under the action of an external force, it may be restricted into a straight line configuration or any other shapes, and would be recovered into the preset shape through bending and twisting if the external force is withdrawn. The elastic deformation section 51 may be made of any material which is commonly used in this industry and has a shape memory function. The present disclosure does not limit specific materials, and materials which are applicable for use in the human body and which have shape memory function are acceptable. In this embodiment, the elastic deformation section 51 is made of a nickel-titanium alloy. To be more specific, a machining method of an elastic deformation section 51 includes: first, cutting a section of hollow nickel-titanium tube having a diameter of about 0.5 to 2.0 mm and a wall thickness of 0.01 to 0.4 mm with laser; then bending the cut nickel-titanium tube with a die into a shape of an elastic deformation section 51 as shown in FIG. 5; and finally, performing thermal treatment for modeling, thus obtaining the elastic deformation section 51.

Figure 7:
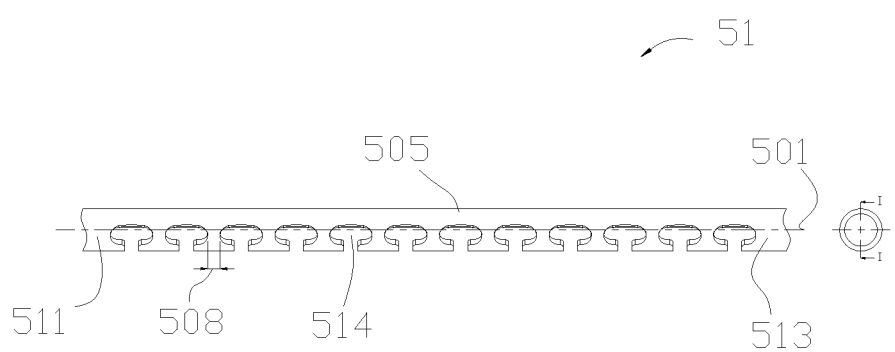
FIG. 7 is a sectional view of an elastic deformation section of the implant as shown in FIG. 5.
Figure 8:
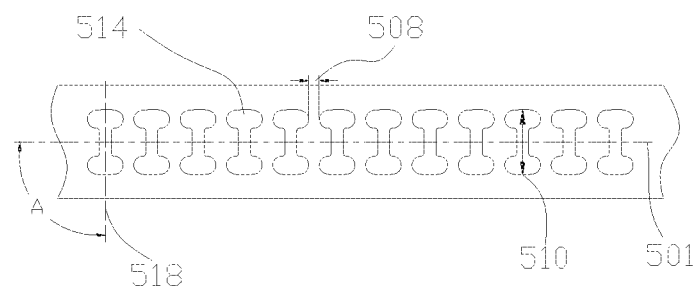
FIG. 8 is a schematic diagram of a groove obtained by splitting and unfolding the elastic deformation section of the implant in FIG. 5 along its lengthwise direction.

With reference to FIG. 7 and FIG. 8 together, in this embodiment, for the purpose that the elastic deformation section 51 may extend into a thinner bronchus to achieve a better squeezing effect on a corresponding tissue, preferably the elastic deformation section 51 is made of a conical nickel-titanium tube having a consistent inner diameter and a gradually varying wall thickness; for example, a conical nickel-titanium tube having an inner diameter of 0.8 to 1.0 mm and a wall thickness varying from 0.01 mm at the distal end to 0.4 mm at the proximal end. Multiple dumbbell-shaped grooves 514 are formed in the nickel-titanium tube, and an extending direction 518 (namely an incision direction) of these grooves 514 and the axial line 501 of the elastic deformation section 51 form a certain angle A, which is preferably 10 to 90 degrees. A gap 508 of about 0.05 to 0.5 mm is provided between every two adjacent grooves 514. It should be understood that as the elastic deformation section 51 has the multiple grooves 514, its bending resistance may vary with changes of the lengths 510 of the grooves 514 along their extending direction 518. A person skilled in the art could set the lengths 510 of the grooves 514 of the elastic deformation section 51 in their extending direction 518 according to an actual clinical requirement to achieve an objective that the bending resistance of the flexible guide section 53 is lower than that of the elastic deformation section 51.

Figure 9:
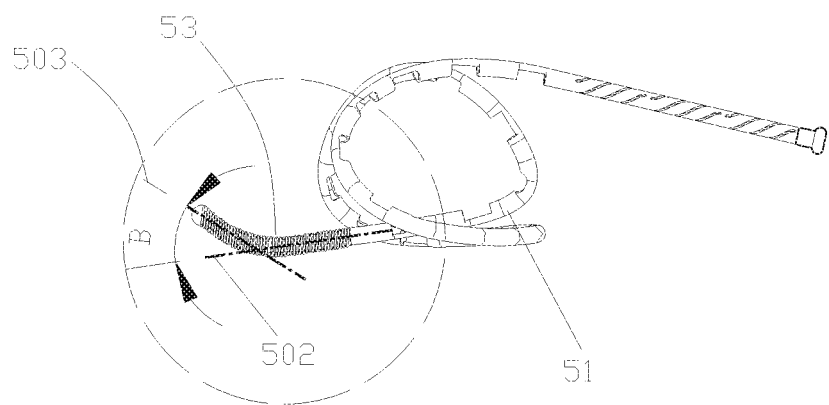
FIG. 9 is a schematic diagram of the implant in FIG. 5 shown without a film.
Figure 10:
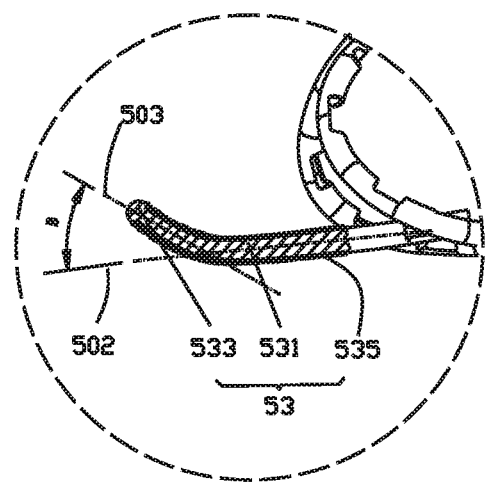
FIG. 10 is an enlarged view of a part inside a ring in FIG. 9.

With reference to FIG. 9 and FIG. 10 together, the flexible guide section 53 is disposed at the distal end of the elastic deformation section 51, and is configured to play a guiding role for the elastic deformation section 51, and under the action of the same external force, the flexible guide section 53 deforms easily in an increasing manner from the proximal end to the distal end. The axial line 503 at the distal end of the flexible guide section 53 and the axial line 502 at the distal end 511 of the elastic deformation section 51 form an included angle B which may be 5 to 60 degrees. In this embodiment, the flexible guide section 53 includes a main body portion 531, a flexible guide section head end 533 disposed at the distal end of the main body portion 531 and a spring 535 disposed on the outer wall of the main body portion 531.

The main body portion 531 may support the spring 535, and may be made of a metal with relatively high elasticity, such as a nickel-titanium alloy and a cobalt-chromium alloy, and the outer diameter of the main body portion 531 is gradually increased from the distal end of the main body portion 531 to the proximal end of the main body portion 531. The proximal end of the main body portion 531 is connected with the distal end 511 of the elastic deformation section 51 through macromolecular heat-shrink tube or film wrapping, glue adhesion, laser welding, soldering and the like. In this embodiment, the main body portion 531 is a solid nickel-titanium rod. It should be understood that the main body portion 531 also may be a hollow nickel-titanium tube. As a hollow nickel-titanium tube, if the inner diameter of the main body portion 531 does not change from the proximal end to the distal end, its outer diameter is gradually increased from the distal end to the proximal end, and if the outer diameter of the main body portion 531 does not change from the proximal end to the distal end, its inner diameter is gradually decreased from the distal end to the proximal end.

In this embodiment, the distal end of the spring 535 and the distal end of the main body portion 531 are fused together at high temperature, thus forming the flexible guide section head end 533. The flexible guide section head end 533 is coaxial with the distal end of the main body portion 531 and closes the distal end of the main body portion 531. The flexible guide section head end 533 may further have an imaging label (not shown in the figures).

The spring 535 is formed by winding a metal wire with a diameter of 0.05 to 0.5 mm (preferably, a tungsten metal wire, a tantalum metal wire and the like with relatively high X-ray developing property). It should be understood that the flexible guide section head end 533, the spring 535 and the main body portion 531 may be formed separately as well, and then the flexible guide section head end 533, and the distal end of the spring 535 are connected together with the distal end of the main body portion 531 through macromolecular heat-shrink tube or film wrapping, glue adhesion, laser welding and the like; in case of separate forming, preferably the flexible guide section head end 533 is made of a metal with relatively high X-ray developing property, such as tungsten and tantalum. It further should be understood that the flexible guide section head end 533 may be removed as required.

It further should be understood that if there is no flexible guide section head end 533, and the main body portion 531 is a hollow nickel-titanium tube, on one hand, a closing member made of the same material or a similar material as the guide head 533 may be disposed in the proximal end of the main body portion 531 to fully close or half-close the distal end of the elastic deformation section 51; on the other hand, the proximal end of the main body portion 531 may be also communicated with the elastic deformation section 51; and at this moment, the implant 500 opens at both the proximal end and the distal end. In any case, it is only necessary to ensure that a core wire (specifically described below) does not penetrate through the distal end of the flexible guide section 53; in other words, when the implant 500 opens at the distal end, it is necessary to ensure that the core wire may enter the implant 500 and the outer diameter of the core wire would be larger than that of an incircle of the opening in the distal end of the implant 500 (when the opening is a non-circular opening, such as a triangular opening and a square opening) or larger than that of the opening in the distal end (when the opening is a circular opening).

Figure 11:
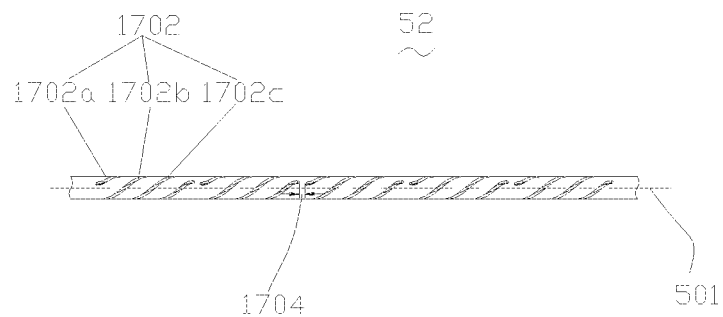
FIG. 11 is a schematic diagram of a connection section of the implant in FIG. 5.
Figure 12:
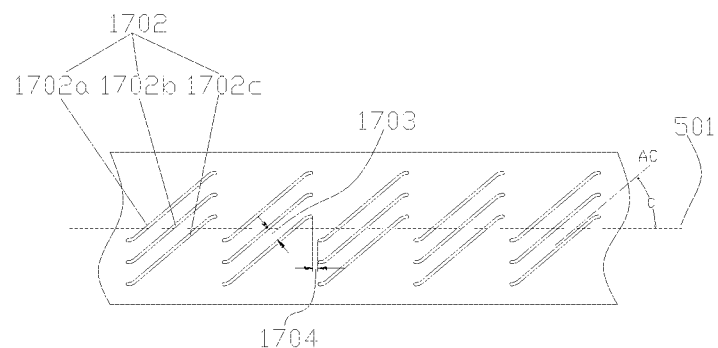
FIG. 12 is a schematic diagram of the connection section, which is split and unfolded along its lengthwise direction, in FIG. 11.

With reference to FIG. 11 and FIG. 12 together, the connection section 52 is connected between the connection member 57 and the elastic deformation section 51, and under the action of the same external force, the bending resistance of the connection section 52 is lower than that of the elastic deformation section 51 (namely, under the action of the same external force, the connection section 52 deforms more easily than the elastic deformation section 51). In this embodiment, multiple groove groups 1702 are disposed on the connection section 52. After the connection section 52 is split along an axial direction and then flattened, it can be seen that each groove group 1702 includes three grooves 1702a, 1702b and 1702c which are arrayed in a circumferential direction of the connection section 52 and are parallel to one another, and the two ends of the three grooves are aligned with each other in the circumferential direction. A certain gap 1703 is provided between every two adjacent grooves in each groove group 1702, and a gap 1704 is provided between every two adjacent groove groups 1702. Each groove is of a slender structure, and the extending direction AC of the multiple grooves and the axial line 501 of the connection section 52 form a certain included angle C. The bending resistance of the entire connection section 52 may be adjusted by adjusting the number of the grooves in each groove group 1702, the sizes of the gaps 1703, the size (degree) of the included angle C between the extending direction AC of the grooves and the axial line 501 of the elastic deformation section 51, and the size of the gap 1704 between every two adjacent groove groups 1702, so that the bending resistance of the connection section 52 is lower than that of the elastic deformation section 51. In other embodiments, there may be 2 to 6 grooves in each groove group 1702, the gap 1703 between every two adjacent grooves in each groove group 1702 may be 0.05 to 1 mm, the included angle C may be 10 to 85 degrees, and the gap 208 between every two adjacent groups may be 0.1 to 1.0 mm. The outer diameter of the elastic deformation section 51 is about 1.0 to 2.0 mm, and the wall thickness is 0.05 to 0.3 mm. Connection between the connection section 52 and the elastic deformation section 51 may be realized via macromolecular heat-shrink tube or film wrapping, glue adhesion, laser welding, soldering and the like. Using conventional techniques, an integrated cutting method is preferred; that is, the elastic deformation section 51 and the connection section 52 which have different texture features are cut from different regions on the same tube material.

Figure 13:
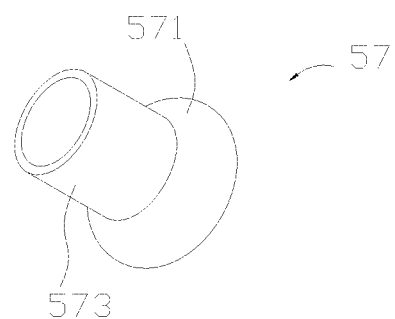
FIG. 13 is a schematic diagram of a connection member of the implant in FIG. 5.
Figure 14:
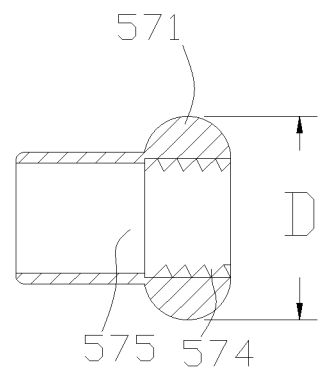
FIG. 14 is a sectional view of the connection member in FIG. 13.
Figure 15:
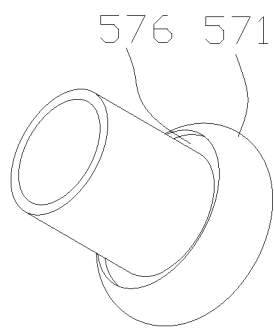
FIG. 15 is a schematic diagram showing the deformation of the connection member in FIG. 13.
Figure 16:
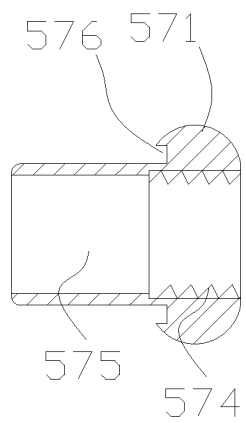
FIG. 16 is a sectional view of the connection member in FIG. 15.

With reference to FIG. 13 and FIG. 14 together, the connection member 57 is disposed at the proximal end of the connection section 52, and includes a protuberance 571 and a connection portion 573. The outer diameter D of the protuberance 571 is larger than that of a portion, which is close to the protuberance 571, on the elastic implant 500 in a delivery state. In this implementation mode, the outer diameter of the portion, which is close to the protuberance 571, on the elastic implant 500 is the outer diameter of the proximal end of the connection section 52. An internal thread 574 is in the protuberance 571. The connection portion 573 is disposed between the protuberance 571 and the connection section 52, and has a cavity 575 which penetrates through the end surfaces of the proximal end and the distal end of the connection portion 573. In this embodiment, the cross section of the protuberance 571, which is parallel to a longitudinal central axis of the protuberance 571, includes two opposite semicircles, and the outer diameter D would not exceed 2.8 mm, preferably 2.0 to 2.3 mm. The protuberance 571 effectively enlarges a contact area of the proximal end of the elastic implant 500, and reduces the injury to a lung tissue during the implantation of the elastic implant 500. It should be understood that the end surface of part of the distal end of the protuberance 571 is sunken towards the proximal end of the protuberance 571, thereby forming an annular recess 576 (see FIG. 15 and FIG. 16) surrounding the longitudinal central line of the protuberance 571 to provide a buckling position for a biopsy forceps which may clamp a connection device more effectively to recycle the elastic implant 500.

With reference to FIG. 5 and FIG. 6 together, the elastic implant film 55 completely wraps the outer surface of the elastic implant 500 except for the protuberance 571, and each groove 514 is filled with the film, but the film does not block the lumen of the elastic implant 500, thereby ensuring that the elastic implant film 55 firmly wraps the elastic implant 500 and also ensuring that the lumen of the elastic implant 500 is unblocked. The elastic implant film 55 may have a thickness of 0.01 to 0.8 mm, and may be prepared from macromolecular solutions featuring high chemical stability, water resistance and weather aging resistance, good low compressibility, good biocompatibility, high mechanical strength, non-toxicity, odorlessness and the like. For example, these macromolecular solutions may be silicone rubber or polyurethane solutions. As the elastic implant film 55 is combined with a metal matrix, the end portion of its proximal end would turn up and fall off most easily under an external force; the outer diameter of the protuberance 571 is larger than that of the portion which is close to the protuberance 571, on the elastic implant 500 in the delivery state, so that the protuberance 571 may protect the end portion of the proximal end of the elastic implant film 55 from being in contact with a tube wall in delivery and withdrawal processes, thereby protecting the elastic implant film 55 from turning up and falling off in the delivery and withdrawal processes.

Figure 17:
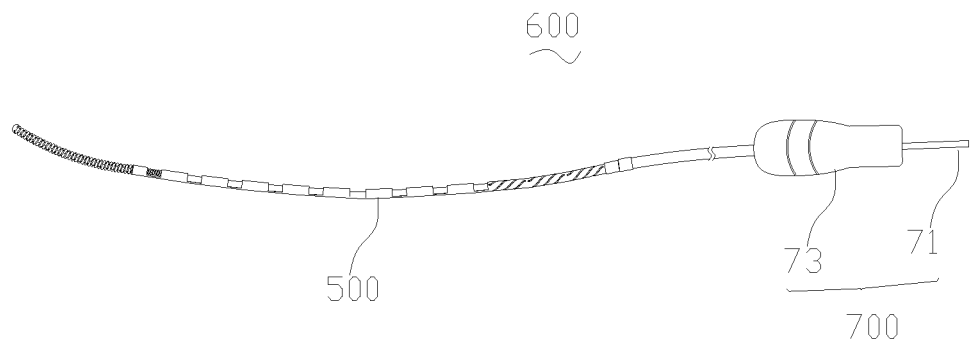
FIG. 17 is a schematic diagram of a lung volume reduction device provided by one embodiment of the present disclosure.
Figure 18:
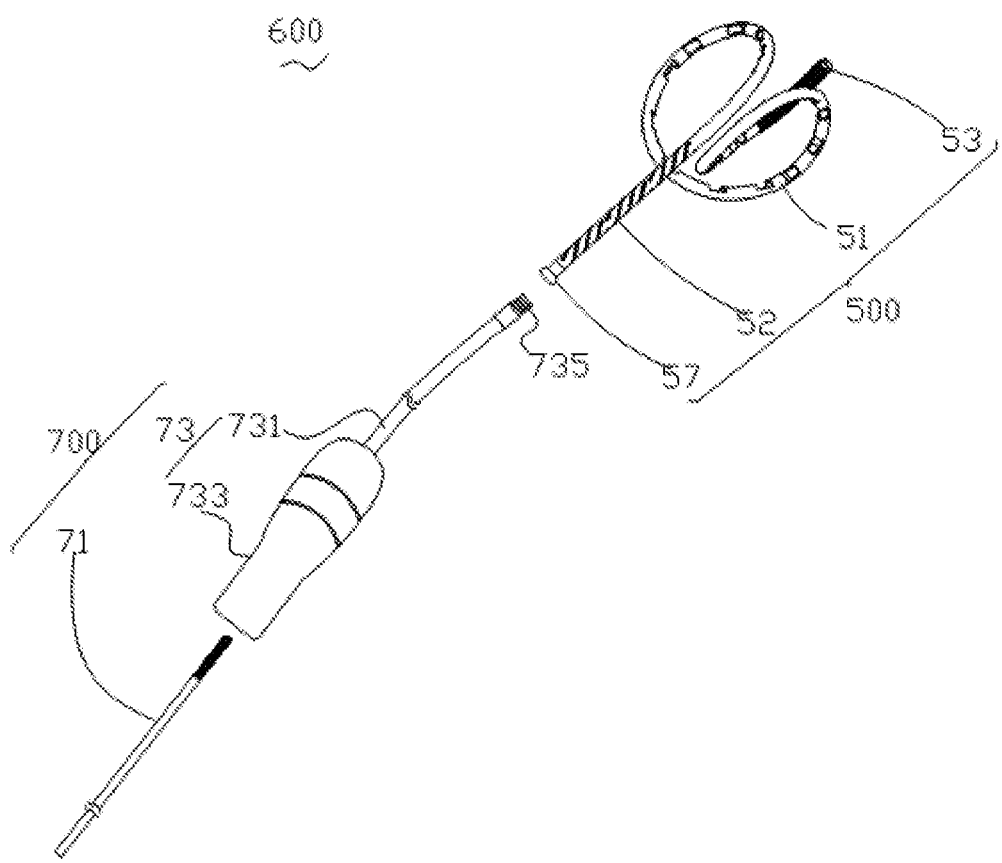
FIG. 18 is a schematic diagram showing decomposition of the lung volume reduction device in FIG. 17.

With reference to FIG. 17 and FIG. 18 together, a lung volume reduction device 600 provided by one embodiment of the present disclosure includes an elastic implant 500 and a delivery device 700. The delivery device 700 includes a core wire 71 and a pushing mechanism 73.

The core wire 71 is accommodated in a lumen of the elastic implant 500, and is configured to limit the elastic implant 500 in an approximately straight-line type delivery state to facilitate delivery of the implant 500 to a lesion portion, thus no delivery sheath is needed to restrict the implant 500, which prevents the delivery sheath from injuring a trachea during a delivery process and further reduces incidence of pneumothorax. The core wire 71 may be made of a section of metal wire having a diameter of 0.1 to 1.1 mm. Compared with the prior art, the present disclosure does not need the delivery sheath, so that the implant 500 may be implanted into a lung bypass or the ends of some small-diameter tracheas to achieve a better treatment effect.

Figure 19:
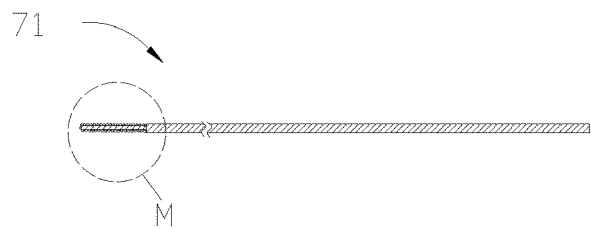
FIG. 19 is a schematic diagram of a core wire of the lung volume reduction device in FIG. 17.
Figure 20:
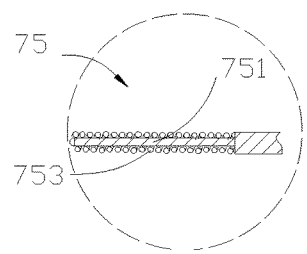
FIG. 20 is an enlarged view of a portion M in FIG. 19.
Figure 21:
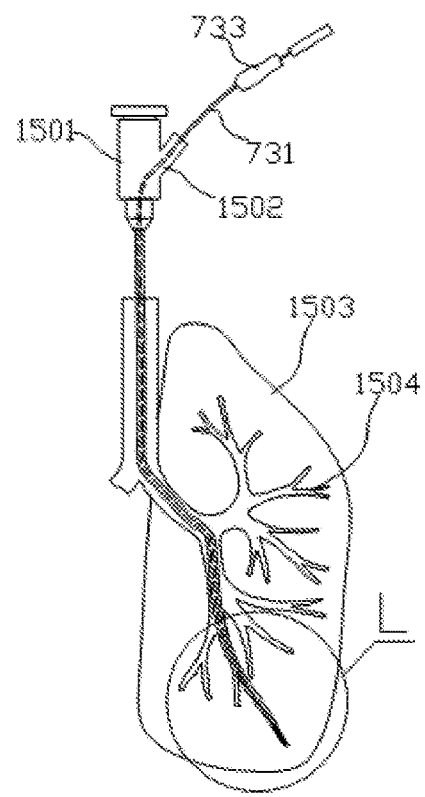
FIG. 21 is a schematic diagram showing the building of a working channel of a lung volume reduction device provided by one embodiment of the present disclosure.
Figure 22:
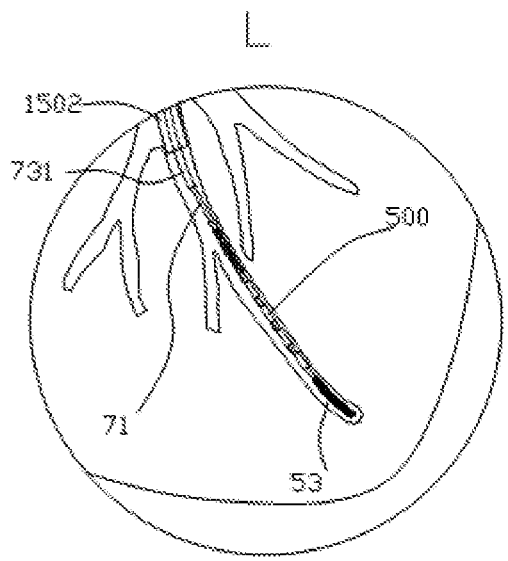
FIG. 22 is an enlarged view of a portion L in FIG. 21.
Figure 23:
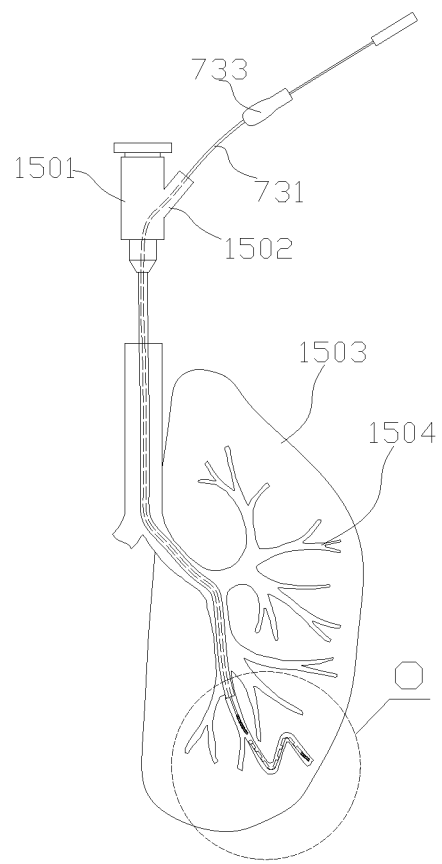
FIG. 23 is a schematic diagram of an implant released.
Figure 24:
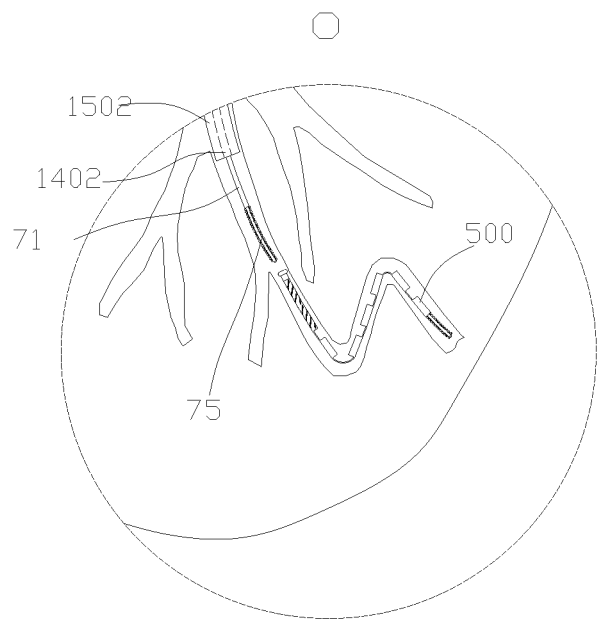
FIG. 24 is an enlarged view of a portion O in FIG. 23.

With reference to FIG. 19 and FIG. 20 together, for the purpose of safety and convenience during operation, a flexible core wire guide head 75, which is coaxial with the core wire 71 and has an imaging label, needs to be disposed at the distal end of the core wire 71. The outer diameter of the core wire guide head 75 is consistent with that of the core wire 71. The core wire guide head 75 includes a guide post 751 and a spring 753 fixed outside and surrounding the guide post 751. The guide post 751 and the core wire 71 can be made in one piece in an integrated structure, or the guide post 751 is fixedly connected to the distal end of the core wire 71; and the spring 753 has an imaging label.

The core wire guide head 75 is configured to guide the core wire 71 to successfully enter the lumen of the elastic implant 500. The flexible core wire guide head 75 may be implemented through a flexible spring, and the spring 753 can surround the guide post 751 which is of an integrated structure with the core wire 71 or is fixedly connected to the distal end of the core wire 71. A specific manufacturing method may include: first thinning the head end of the core wire 71 to manufacture the guide post 751, and then fixing a section of the spring 753 having a length of 5 to 150 mm outside the guide post 751. The spring 753 and the core wire 71 may be fixed via macromolecular heat-shrink tube or film wrapping, glue adhesion, laser welding, soldering and the like. Under the guidance of the flexible core wire guide head 75, the core wire 71 may successfully enter the lumen of the implant 500 from the proximal end of the implant 500 to restrict the implant 500 into an approximate straight line configuration (as shown in FIG. 17) from the shape as shown in FIG. 5 and FIG. 9.

In this embodiment, with the flexible guide section 53, the implant 500 equipped with a core wire 71 further has a function of exploring a path in the bronchus to reach the lesion region. An imaging label needs to be provided on the core wire guide head 75 to guide and monitor the operation condition of the core wire 71 in the lung. The imaging label can display the implant through a fluorescence inspection system, an ultrasonic imaging system, an MRI (Magnetic Resonance Imaging) system, an X-ray CT (Computerized Tomography) system or other remote imaging systems, and there is no limitation to a specific structure. The core wire is developed and guided through these systems. In this embodiment, the spring formed by winding a metal wire with the wire diameter of 0.01 to 0.3 mm and relatively high X-ray developing property, such as a tungsten metal wire and a tantalum metal wire, is used as an imaging label. In this embodiment, the imaging label and the core wire guide head 75 are combined into one component to realize two functions. Besides such a mode, an extra developing label may be disposed on the core wire guide head 75. Of course, when the surface of the implant of the present disclosure is not wrapped by an elastic film, and the implant is made of a material capable of facilitating imaging by itself, such as the nickel-titanium alloy, no imaging label is disposed.

The pushing mechanism 73 includes a hollow pushing member 731 and a control handle 733 connected with the hollow pushing member 731. The hollow pushing member 731 and the implant 500 surround the core wire 71 in sequence from outside to inside; and the distal end of the hollow pushing member 731 is detachably connected with the proximal end 511 of the implant 500. In this embodiment, the hollow pushing member 731 is a pushing steel cable, and a connection matching member 735 having an external thread matched with the internal thread of the connection member 57 is disposed at its distal end. During assembly, the internal thread of the connection member 57 is in threaded connection with the connection matching member 735 with the external thread of the pushing mechanism 73, and the implant 500 may be reliably fixed at the distal end of the hollow pushing member 73. After an implant 500 is pushed to a corresponding position of the bronchus, the connection member 57 of the implant 500 is screwed out of and separated from the connection matching member 735 of the hollow pushing member 73 by twisting the control handle 733 of the hollow pushing member 73. The connection member 57 and the connection matching member 735 may be embodied in the form of other detachably fixed connection components, such as magnetic connection devices, elastic buckles and ropes, which are disposed on the implant 500 and the hollow pushing member 103, respectively, to realize a detachable connection.

Assembly steps of the elastic implant 500 and the core wire 71, as well as the hollow pushing member 731, are as follows: first, connecting the elastic implant 500 with the connection matching member 735 at the distal end of the hollow pushing member 731 through the threads to communicate the hollow pushing member 731 with an inner channel of the elastic implant 500; and then pushing the core wire 71 into the elastic implant 500 along a channel of the hollow pushing member 731 to restrict the elastic implant 500, which is curled in a natural state, into a tube in an approximately straight line type delivery state.

With reference to figures from FIG. 21 to FIG. 24, an implant 500 equipped with the core wire 73 and the hollow pushing member 731 is delivered into the bronchus 1504 of a lung 1503 through a working channel 1502 of a bronchoscope 1501. With the assistance of X-rays, the implant 500 is pushed to an expected position by using the hollow pushing member 731, and then the core wire 71 is withdrawn. During withdrawal of the core wire 71, the implant 500 is automatically recovered to the natural shape as shown in FIG. 17 from the straight line type delivery state restricted by the core wire 71; and in this recovery process, the pulmonary emphysema region may be squeezed and pulled, and a relatively healthy lung tissue therearound may exert a better respiration physiological function, thereby achieving a lung volume reduction effect. The threaded connection between the connection matching member 735 at the distal end of the hollow pushing member 731 and the connection member 57 of the elastic implant 500 is relieved by rotating the handle 733, thereby releasing the implant 500.

Figure 25:
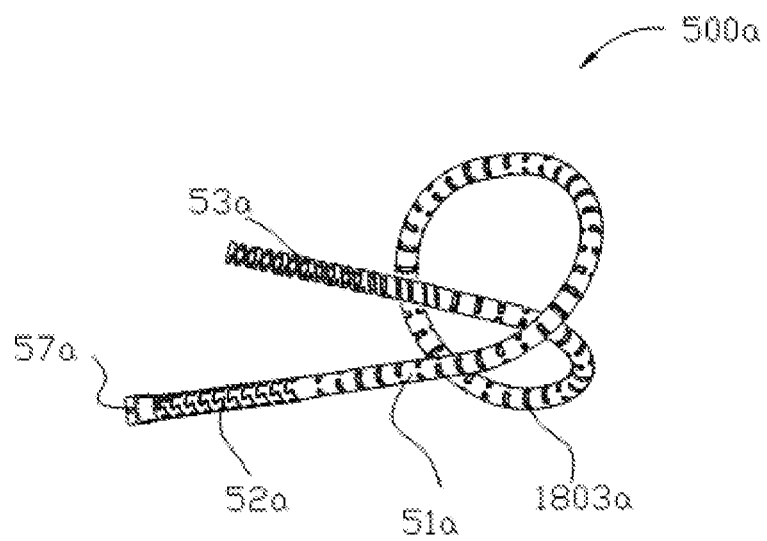
FIG. 25 is a schematic diagram of an implant provided by another embodiment of the present disclosure.

With reference to FIG. 25, an elastic implant 500a provided by another embodiment of the present disclosure includes a hollow tubular elastic deformation section 51a, a flexible guide section 52a connected with the distal end of the elastic deformation section 51a, a connection section 52a connected with the proximal end of the elastic deformation section 51a, and a connection member 57a connected with the proximal end of the connection section 54a. The implant 500a is opened at least at the proximal end, and the elastic deformation section 51a and the flexible guide section 52a may be formed in one piece in an integrated structure, or are fixedly connected with each other. The distal end of the flexible guide section 52a is the distal end of the elastic implant 500a. Under the action of the same external force, the flexible guide section 52a deforms more easily than the elastic deformation section 51a (i.e., under the action of the same external force, the bending resistance of the flexible guide section 52a is lower than that of the elastic deformation section 51a), so that it may move better in a bronchus without injuring a surrounding tissue.

Figure 26:
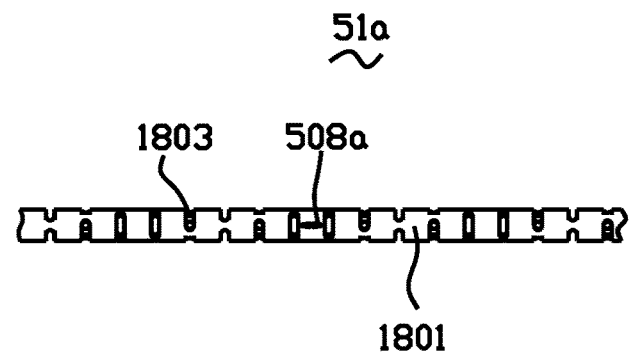
FIG. 26 is a schematic diagram of an elastic deformation section of the implant in FIG. 25.
Figure 27:
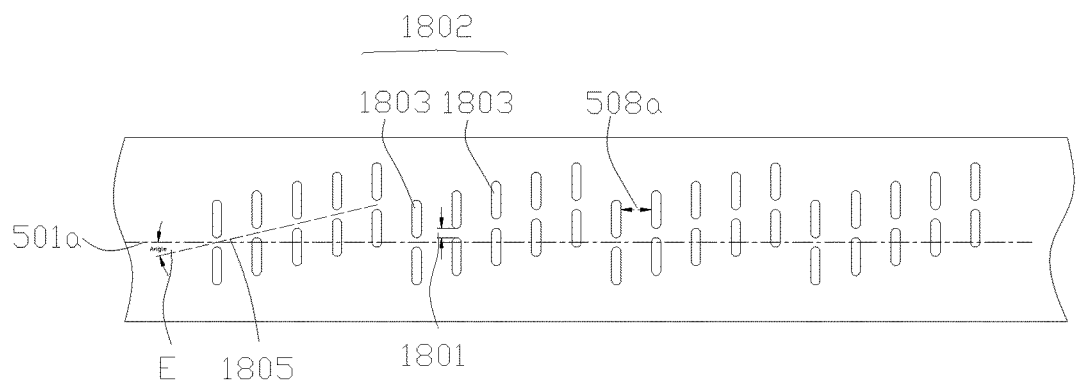
FIG. 27 is a schematic diagram of the elastic deformation section, which is split and unfolded along its lengthwise direction, in FIG. 26.

With reference to FIG. 26 and FIG. 27 together, the elastic deformation section 51a includes multiple groove clusters 1802 which are arrayed in an axial direction of the elastic deformation section 51a in a spaced-apart manner. Each groove cluster 1802 consists of five elliptical groove groups 1803 which are disposed side by side and are arrayed in a stair-stepping manner. Each groove group 1803 in this embodiment consists of two side-by-side grooves; a certain gap 1801 is provided between the two grooves in each groove group 1803; and the long axis of each groove is perpendicular to the axial line of the elastic deformation section 51a. The extending direction 1805 of the arrangement of every two groups in each groove cluster 1802 and the axial line 501a of the elastic deformation section 51a form a certain included angle E which may be 60 to 90 degrees. A gap 508a of about 0.3 to 5 mm is provided between every two adjacent groove groups 1803 in each groove cluster 1802. The groove groups 1803 arrayed in the stair-stepping manner contribute to the bending of the elastic deformation section 51a into a specific shape. A portion having a length of about 0.5 to 5 mm at the proximal end of the elastic deformation section 51a is cut into a threaded trench serving as a connection member 57a. A cut nickel-titanium tube is bent with a die into a shape as shown in FIG. 25, and then is subjected to thermal treatment modeling, thereby forming the elastic deformation section 51a of an elastic implant 500a.

Figure 28:
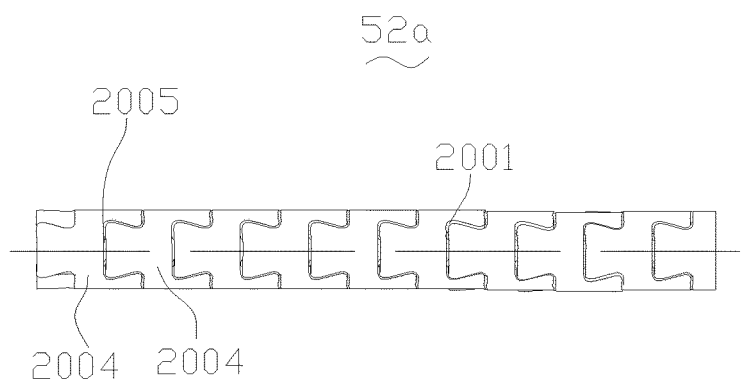
FIG. 28 is a schematic diagram of a connection section of the implant in FIG. 25.
Figure 29:
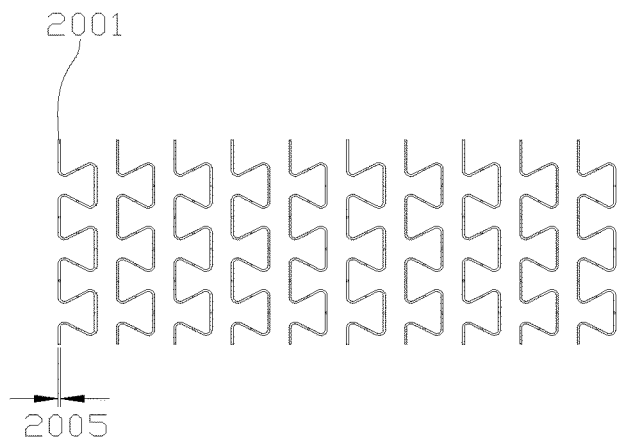
FIG. 29 is a schematic diagram of the connection section, which is split and unfolded along its lengthwise direction, in FIG. 28.
Figure 30:
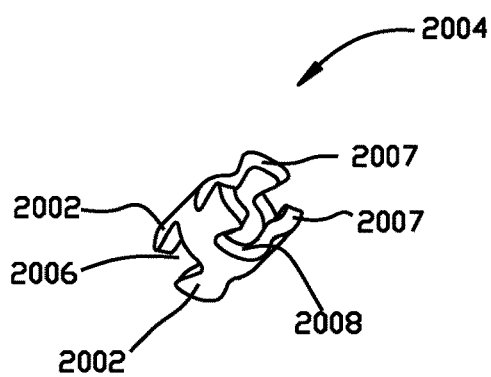
FIG. 30 is a schematic diagram of a connection subcomponent of the connection section in FIG. 28.

Under the action of the same external force, the bending resistance of the connection section 52a is lower than that of the elastic deformation section 51a to more effectively reduce injury of the connection section 52a to a bronchus wall. With reference to the Figures from FIG. 28 to FIG. 30, in this embodiment, the connection section 52a is a tubular body which is formed by connecting multiple hollow subcomponents 2004 in an end-to-end manner and has multiple circumferentially continuous wavy grooves 2001. The grooves 2001 have a certain width 2005 which may be preferably 0.01 mm to 0.3 mm. The starting points and ending points of every two adjacent wavy grooves 2001 are overlapped in the circumferential direction of the connection section 52a. Preferably, in this embodiment, the proximal end of each subcomponent 2004 includes multiple proximal end bulges 2002 distributed in the circumferential direction of the hollow subcomponent 2004 in an equally-spaced manner; and the circumferential length of each proximal end bulge 2002 is gradually decreased from the proximal end to the distal end, thereby forming a dovetail-shaped opening towards a proximal end recess 2006 at the proximal end between every two adjacent proximal end bulges 2002; the distal end of each hollow subcomponent 2004 includes multiple distal end bulges 2007 distributed in the circumferential direction of the hollow subcomponent 2004 in an equally-spaced manner; and the circumferential length of each distal end bulge 2007 is gradually increased from the proximal end to the distal end, thereby forming a dovetail-shaped opening towards a distal end recess 2008 at the distal end between every two adjacent distal end bulges 2007; the number of the proximal end bulges 2002 of each hollow subcomponent 2004 is equal to that of the distal end bulges 2007 of the same hollow subcomponent 2004; and one distal end recess 2008 on each hollow subcomponent 2004 is aligned with one proximal end bulge 2002 on the same hollow subcomponent 2004. Therefore, in two hollow subcomponents 2004, the multiple dovetail-shaped proximal end bulges 2002 on one hollow subcomponent 2004 mesh with the multiple distal end recesses 2008 of the other hollow subcomponent 2004, so that the two separated hollow subcomponents 2004 form an interlocked structure, and the multiple hollow subcomponents 2004 are spliced and combined to form the connection section 52a, As all the separated subcomponents 2004 are connected through meshing structures of the dovetail-shaped bulges and the dovetail recesses, the connection section 52a with such structure has extremely high flexibility and connection strength, and may transmit a torque to the elastic deformation section 51a at a ratio of 1 to 1 during twisting of the connection member 57. Using conventional techniques, the subcomponents 2004 may be also machined in other ways, such as machining, casting and powder metallurgy. It should be understood that the connection section 52a has extremely high flexibility and extremely low bending resistance, so that the objective that the bending resistance of the connection section 52a be lower than that of the elastic deformation section 51a may be achieved easily by adjusting the bending resistance of the elastic deformation section 51a, It should be understood that the multiple proximal end bulges 2002 may be also distributed at the proximal ends of the subcomponents 2004 in a non-equally spaced manner to achieve the objective that the multiple subcomponents 2004 may be spliced together.

Figure 31:
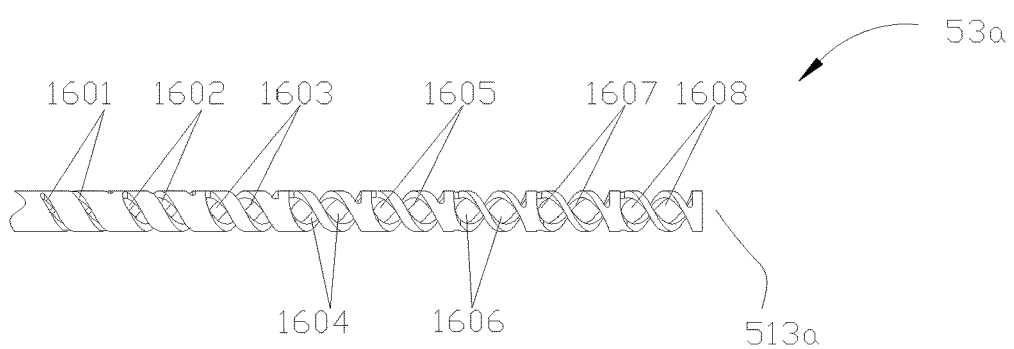
FIG. 31 is a schematic diagram of a flexible guide section of the implant in FIG. 25.
Figure 32:
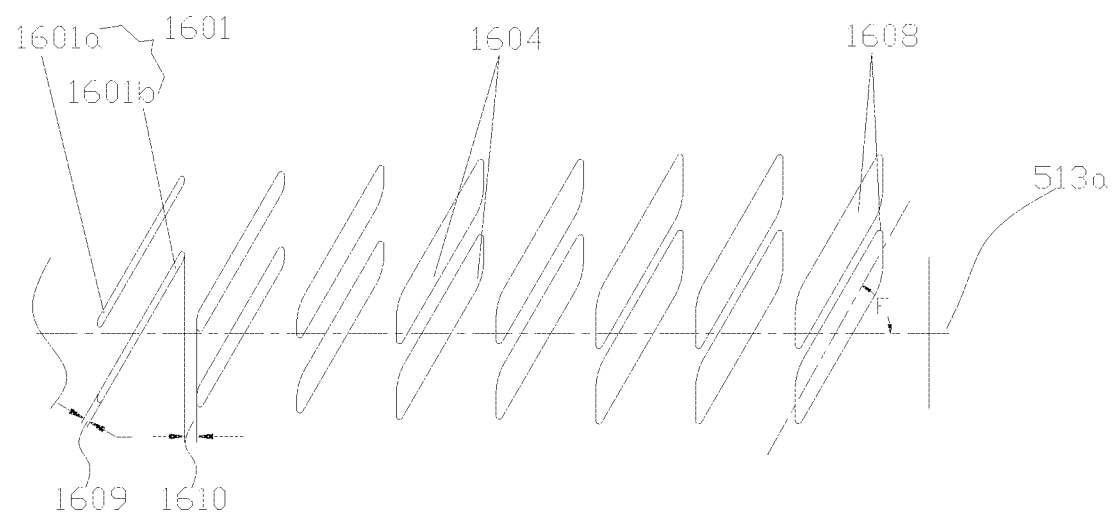
FIG. 32 is a schematic diagram of the flexible guide section, which is split and unfolded along its lengthwise direction, in FIG. 31.

Under the action of the same external force, the bending resistance of the flexible guide section 52a is lower than that of the elastic deformation section 51a, so as to guide the elastic deformation section 51a better to move in the bronchus and reduce injury to the bronchus wall. Under the action of the same external force, the bending resistance of the flexible guide section 52a is gradually enhanced from the distal end to the proximal end. With reference to FIG. 31 and FIG. 32 together, in this embodiment, the flexible guide section 52a is a tubular body, which is cut from a nickel-titanium tube through laser and has grooves, and under the action of the same external force, its bending resistance is gradually enhanced from the distal end to the proximal end (i.e., under the action of the same external force, its deformability is gradually lowered from the distal end to the proximal end, and it becomes harder from the distal end to the proximal end), so as to achieve a better guide effect on the elastic implant 500a. It should be understood that as the flexible guide section 52a is the tubular body having the multiple grooves, its bending resistance may change with the change of a gap between every two adjacent grooves. A person skilled in the art could set the gap between every two adjacent grooves according to an actual clinical requirement to achieve the objective that the bending resistance of the flexible guide section 52a is lower than that of the elastic deformation section 51a.

The flexible guide section 52a includes multiple slender groove groups from 1601 to 1608. Each groove group (for example 1601) consists of two or more parallel grooves 1601a and 1601b, and each parallel groove has a certain width 1609. The extending direction of these groove groups from 1601 to 1608 and the axial line 512a of the flexible guide section 52a form a certain angle F. A gap 1610 is provided between every two adjacent groove groups. The bending resistance of the flexible guide section 52a may be adjusted by adjusting the number and the widths 1609 of the grooves in each groove group, the degree size of the angle F, and the sizes of the gaps 1610. Preferably, there are 2 to 6 parallel grooves 1601, the gaps 1609 are 0.05 to 1 mm, the angle F is 5 to 85 degrees, and the gaps 1610 is 0.1 to 1.0 mm. The parallel groove groups (from 1601 to 1608) with different widths 1609 are combined into a same nickel-titanium tube, thereby achieving the objective that under the action of the same external force, the bending resistance of the flexible guide section 52a is gradually enhanced from the distal end to the proximal end; and the flexible guide section 52a with a bending resistance that gradually changes may achieve a better guide effect on the elastic implant 500a.

The flexible guide section 52a and the elastic deformation section 51a may be connected via macromolecular heat-shrink tube or film wrapping, glue adhesion, laser welding, soldering and the like. Using conventional techniques, an integrated cutting technique is preferred: cutting the flexible guide section 52a and the elastic deformation section 51a which have different texture features from different regions on the same tube material. For the purpose of achieving a bending resistance that has a gradual change on the flexible guide section 53a, one feasible mode is to keep the angle F between every two adjacent groove groups unchanged and gradually decrease the widths 1609 of the grooves from the distal end to the proximal end, and another feasible mode is to keep the widths 1609 of the grooves in every two adjacent groove groups unchanged and gradually enlarge the angle F. It should be understood that the effect of gradually enhancing the bending resistance of the flexible guide section 52a from the distal end to the proximal end also may be achieved by simultaneously changing the angle F and the widths 1609 of the grooves in every two adjacent groove groups.

Figure 33:
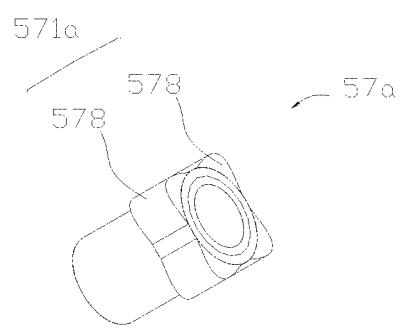
FIG. 33 is a schematic diagram of a connection member of the implant in FIG. 25.
Figure 34:
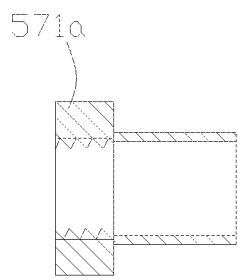
FIG. 34 is a sectional view of the connection member in FIG. 33.
Figure 35:
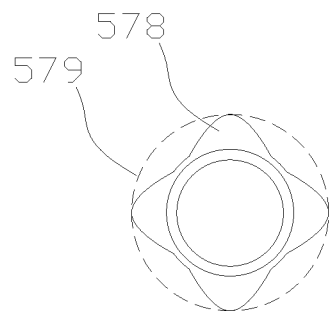
FIG. 35 is a top view of the proximal end side of the connection member in FIG. 33.

With reference to FIG. 33 and FIG. 34, the connection member 57a is substantially the same as the connection body 57, but what is different is that a protuberance 571a of the connection member 57a has multiple small bulges 578 which are distributed in the circumferential direction of the protuberance 571a in an equally-spaced apart manner and are connected with one another. With reference to FIG. 35, the multiple small bulges 578 form a virtual circumference 579 together (i.e., a circumcircle of the multiple small bulges 578 is 579). The diameter of the circumference 579 is the outer diameter of the protuberance 571a, The multiple small bulges 578 provide a buckling position for a biopsy forceps, so that the biopsy forceps may effectively clamp the connection device to recycle the elastic implant 500a. The connection member 57a and the connection section 52a may be connected via macromolecular heat-shrink tube or film wrapping, glue adhesion, laser welding, soldering and the like.

Figure 36:
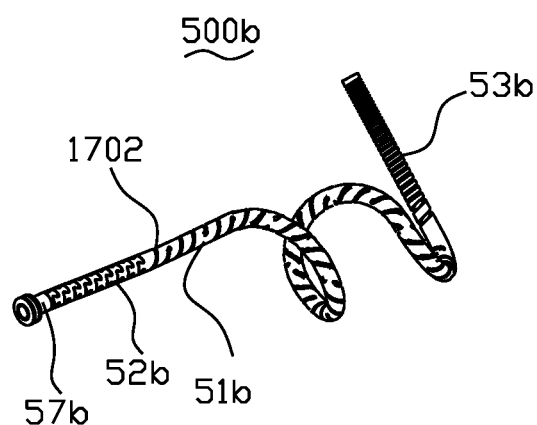
FIG. 36 is a schematic diagram of an elastic implant provided by another embodiment.

With reference to FIG. 36, an elastic implant 500b provided by another embodiment of the present disclosure includes a hollow tubular elastic deformation section 51b, a flexible guide section 53b connected with the distal end of the elastic deformation section 51b, a connection section 52b connected with the proximal end of the elastic deformation section 51b, and a connection member 57b connected with the proximal end of the connection section 52b. The implant 500b is opened at least at the proximal end; the elastic deformation section 51*b* and the flexible guide section 53*b* may be made in one piece in an integrated structure, or are fixedly connected with each other. The distal end of the flexible guide section 53*b* is the distal end of the elastic implant 500*b*. Under the action of a same external force, the flexible guide section 53*b* deforms more easily than the elastic deformation section 51*b*, so that it may move in a bronchus better without injuring a surrounding tissue.

The arrangement mode of the grooves of the elastic deformation section 51*b* is substantially the same as that of the grooves of the connection section 52 of the first embodiment, and no further description will be given here.

Figure 37:
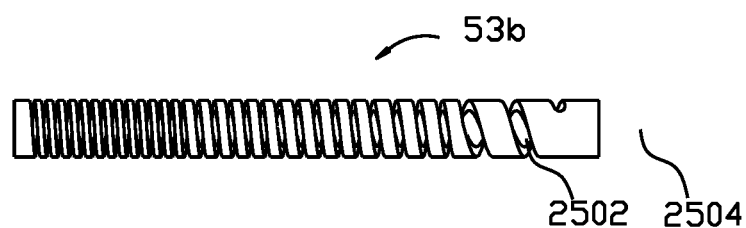
FIG. 37 is a schematic diagram of a flexible guide section of the implant in FIG. 36.
Figure 38:
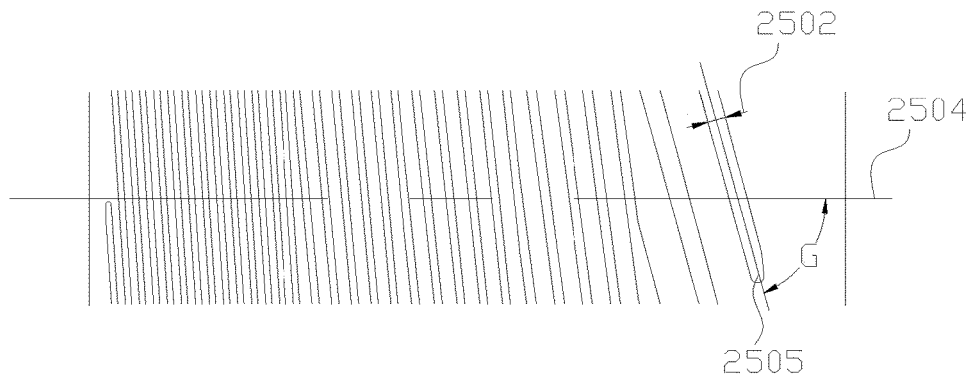
FIG. 38 is a schematic diagram of the flexible guide section, which is split and unfolded along its lengthwise direction, in FIG. 37.

With reference to FIG. 37 and FIG. 38, the flexible guide section 53*b* is a tubular body which is cut from a nickel-titanium tube through laser and has continuous spiral grooves, and under the action of the same external force, its bending resistance is gradually enhanced from the distal end to the proximal end (i.e., under the action of the same external force, its deformability is gradually lowered from the distal end to the proximal end) to achieve a better guide effect on the elastic implant 500*b*. It should be understood that as the flexible guide section 53*b* is a tubular body having continuous spiral grooves, its bending resistance may change with the change of a gap between every two adjacent grooves. A person skilled in the art could set the gap between every two adjacent grooves according to an actual clinical requirement to achieve the objective that the bending resistance of the flexible guide section 53*b* is lower than that of the elastic deformation section 51*b*.

The flexible guide section 53*b* includes the continuous spiral grooves 2502. On an unfolded plane formed by splitting the flexible guide section 53*b* along its axial direction, from the distal end to the proximal end of the flexible guide section 53*b*, the gap between every two adjacent grooves 2502 is gradually increased as well to achieve the objective of gradually enhancing the bending resistance of the flexible guide section 53*b* from the distal end to the proximal end.

It should be understood that on the unfolded plane formed by splitting the flexible guide section 53*b* along its axial direction, from the distal end to the proximal end of the flexible guide section 53*b*, when an included angle G between the extending direction 2505 of the grooves 2502 of the flexible guide section 53*b* and the axial direction 2504 of the flexible guide section 53*b* is unchanged, and the widths of the grooves of the flexible guide section 53*b* along the axial direction 2504 of the flexible guide section 53*b* are gradually decreased, the gap between every two adjacent grooves 2502 is gradually increased as well, and the objective of gradually enhancing the bending resistance of the flexible guide section 53*b* from the distal end to the proximal end may be also achieved.

It should be understood that on the unfolded plane formed by splitting the flexible guide section 53*b* along its axial direction, from the distal end to the proximal end of the flexible guide section 53*b*, when the widths of the grooves of the flexible guide section 53*b* along the axial direction 2504 of the flexible guide section 53*b* are unchanged, and the included acute angle between the extending direction 2505 of the grooves of the flexible guide section 53*b* and the axial direction 2504 of the flexible guide section 53*b* is gradually increased, the gap between every two adjacent grooves 2502 is gradually increased as well, and the objective of gradually enhancing the bending resistance of the flexible guide section 53*b* from the distal end to the proximal end may be also achieved.

The structure of the connection section 52*b* is substantially the same as that of the connection section 52*a*, and no further description will be given here.

Figure 39:
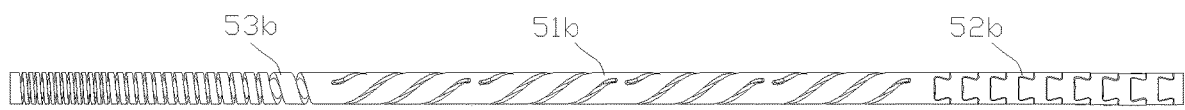
FIG. 39 is a schematic diagram of integration of an elastic deformation section, a flexible guide section and a connection section.

Preferably, a technique of forming in one piece in an integrated manner is adopted. Features of the elastic deformation section 51*b*, the flexible guide section 53*b* and the connection section 52*b* which are cut from the same nickel-titanium tube through laser are as shown in FIG. 39, and problems of low connection strength and the like which are caused by connecting separate pieces mode may be effectively avoided.

Figure 40:
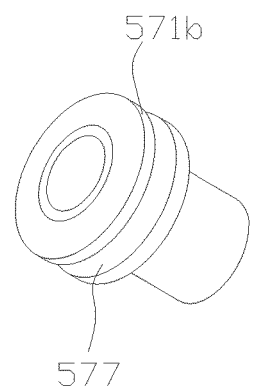
FIG. 40 is a schematic diagram of a connection member of the elastic implant in FIG. 36.
Figure 41:
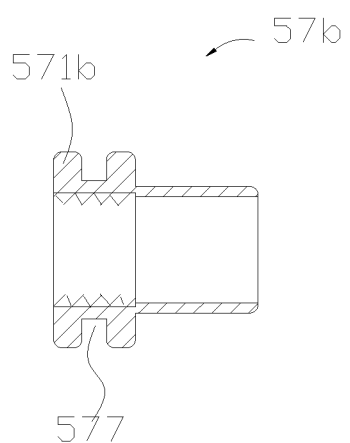
FIG. 41 is a sectional view of the connection member in FIG. 40.

With reference to FIG. 40 and FIG. 41 together, the connection member 57*b* is substantially the same as the connection member 57, but what is different is that part of the side surface of the protuberance 571*b* of the connection member 57*b* is sunken towards the inside of the protuberance 571*b*, thereby forming an annular recess 577 surrounding the longitudinal central line of the protuberance 571*b*.

The above descriptions are made to the embodiments of the present disclosure in combination of drawings, but not intended to limit the present disclosure by the above-mentioned specific implementation modes which are merely schematic, but not restrictive. An ordinary person skilled in the art can also make many implementation modes without departing from the purpose of the present disclosure and the scope claimed by claims under an enlightenment of the present disclosure, and these implementation modes shall all fall within the protection of the present disclosure.

The invention claimed is:

1. A lung volume reduction elastic implant, characterized in that the implant is tubular, is opened at least at the proximal end, and comprises an elastic deformation section, a flexible guide section connected with the distal end of the elastic deformation section, and a protuberance connected with the proximal end of the elastic deformation section; and the elastic deformation section has a lengthwise direction and a shape memory characteristic, and has a plurality of grooves formed in a spaced manner along the lengthwise direction of the elastic deformation section; and each groove is communicated with a lumen of the elastic deformation section; and the outer diameter of the protuberance is larger than that of a portion, which is close to the protuberance, on the elastic implant in a delivery state; and wherein the lung volume reduction elastic implant further comprises a connection section located entirely between the elastic deformation section and the protuberance.

2. The lung volume reduction elastic implant according to claim 1, wherein each groove has an incision direction, and an included angle between the incision direction of each groove and the lengthwise direction of the elastic deformation section ranges from 10 to 90 degrees.

3. The lung volume reduction elastic implant according to claim 2, characterized by further comprising an elastic film that surrounds the outer walls of the elastic deformation section and the flexible guide section.

4. The lung volume reduction elastic implant according to claim 3, characterized in that the grooves are further filled with the elastic film.

5. The lung volume reduction elastic implant according to claim 2, characterized in that the elastic deformation section is made of a conical nickel-titanium tube having an outer diameter that gradually increases from the distal end to the proximal end, and a gap of 0.05 mm to 0.5 mm is provided between every two adjacent grooves of the elastic deformation section.

6. The lung volume reduction elastic implant according to claim 1, characterized in that under the action of the same external force, the flexible guide section deforms more easily in an increasing manner from the proximal end to the distal end.

7. The lung volume reduction elastic implant according to claim 6, characterized in that the flexible guide section comprises a main body portion having a spring on the outer wall; the proximal end of the main body portion is connected with the elastic deformation section; and the outer diameter of the main body portion gradually increases from the distal end to the proximal end.

8. A lung volume reduction elastic implant, characterized in that the implant is tubular, is opened at least at the proximal end, and comprises an elastic deformation section, a flexible guide section connected with the distal end of the elastic deformation section, and a protuberance connected with the proximal end of the elastic deformation section; and the elastic deformation section has a lengthwise direction and a shape memory characteristic, and has a plurality of grooves formed in a spaced manner along the lengthwise direction of the elastic deformation section; and each groove is communicated with a lumen of the elastic deformation section; and the outer diameter of the protuberance is larger than that of a portion, which is close to the protuberance, on the elastic implant in a delivery state; and wherein the flexible guide section comprises a tubular body which is cut from the nickel-titanium tube and has continuous spiral grooves.

9. The lung volume reduction elastic implant according to claim 8, characterized in that the gap between every two adjacent grooves of the flexible guide section along the axial direction of the flexible guide section gradually increases from the distal end to the proximal end of the flexible guide section.

10. The lung volume reduction elastic implant according to claim 1, wherein under the action of the same external force, the connection section deforms more easily than the elastic deformation section.

11. The lung volume reduction elastic implant according to claim 10, characterized in that the connection section has a plurality of grooves formed in a spaced manner along the lengthwise direction of the connection section, and each groove of the connection section communicates with the lumen of the connection section.

12. The lung volume reduction elastic implant according to claim 10, characterized in that the connection section comprises multiple hollow subcomponents connected with one another in an end-to-end manner; the proximal end of each hollow subcomponent comprises multiple proximal end bulges distributed along a circumferential direction of the hollow subcomponent; the circumferential length of each proximal end bulge gradually decreases from the proximal end to the distal end; a proximal end recess is formed between every two adjacent proximal end bulges; the distal end of each hollow subcomponent comprises multiple distal end bulges distributed along the circumferential direction of the hollow subcomponent; the circumferential length of each distal end bulge gradually increases from the proximal end to the distal end; and a distal end recess is formed between every two adjacent distal end bulges.

13. A lung volume reduction elastic implant, characterized in that the implant is tubular, is opened at least at the proximal end, and comprises an elastic deformation section, a flexible guide section connected with the distal end of the elastic deformation section, and a protuberance connected with the proximal end of the elastic deformation section; and the elastic deformation section has a lengthwise direction and a shape memory characteristic, and has a plurality of grooves formed in a spaced manner along the lengthwise direction of the elastic deformation section; and each groove is communicated with a lumen of the elastic deformation section; and the outer diameter of the protuberance is larger than that of a portion, which is close to the protuberance, on the elastic implant in a delivery state; and wherein the end surface of part of the distal end of the protuberance is sunken towards the proximal end of the protuberance, thereby forming an annular recess surrounding the longitudinal central line of the protuberance.

14. The lung volume reduction elastic implant according to claim 1, characterized in that part of the side surface of the protuberance is sunken towards the inside of the protuberance, thereby forming an annular recess surrounding the longitudinal central line of the protuberance.

15. The lung volume reduction elastic implant according to claim 1, characterized in that the protuberance comprises multiple small bulges distributed along the circumferential direction of the protuberance in a spaced manner.

16. A lung volume reduction device, characterized by comprising the implant of claim 1, and a delivery device that is adapted for use with the implant, wherein the delivery device comprises a core wire and a hollow pushing member; the proximal end of the implant is detachably connected to the distal end of the pushing member; and the core wire is extends through and is disposed in a lumen of the implant and a lumen of the pushing member.

17. The lung volume reduction device according to claim 16, characterized in that a core wire guide head coaxial with the core wire is disposed at the distal end of the core wire, and the outer diameter of the core wire guide head is consistent with that of the core wire.

18. The lung volume reduction device according to claim 17, characterized in that the core wire guide head comprises a guide post and a spring that surrounds the guide post; wherein the guide post and the core wire are made in one piece in an integrated structure or the guide post is fixedly connected to the distal end of the core wire; and the spring has an imaging label.

19. The lung volume reduction device according to claim 16, characterized in that the proximal end of the implant is detachably connected with the distal end of the pushing member.

20. The lung volume reduction device according to claim 13, wherein the connection section has a plurality of grooves formed in a spaced manner along the lengthwise direction of the connection section, and each groove of the connection section communicates with the lumen of the connection section.

* * * * *